United States Patent
Culp et al.

(10) Patent No.: US 9,279,810 B2
(45) Date of Patent: Mar. 8, 2016

(54) CELL BINDING PEPTIDES FOR DIAGNOSIS AND DETECTION

(71) Applicant: Affinergy, LLC, Durham, NC (US)

(72) Inventors: William David Culp, Durham, NC (US); Martyn Kerry Darby, Chapel Hill, NC (US); Dalia Isolda Juzumiene, Cary, NC (US); Magdalena Krajewska, Cary, NC (US); Natalia Lygina, Cary, NC (US); Juhua Morrison, Oak Ridge, NC (US); Shrikumar Ambujakshan Nair, Cary, NC (US); William Bourchier Siesser, Durham, NC (US); Danuta Wronska, Raleigh, NC (US)

(73) Assignee: Affinergy, LLC, Durham, NC (US)

( * ) Notice: Subject to any disclaimer, the term of this patent is extended or adjusted under 35 U.S.C. 154(b) by 0 days.

(21) Appl. No.: 14/523,295

(22) Filed: Oct. 24, 2014

(65) Prior Publication Data

US 2015/0125896 A1    May 7, 2015

Related U.S. Application Data

(60) Provisional application No. 61/895,889, filed on Oct. 25, 2013.

(51) Int. Cl.
*C12Q 1/24* (2006.01)
*G01N 33/569* (2006.01)
*C07K 7/08* (2006.01)

(52) U.S. Cl.
CPC ............ *G01N 33/56966* (2013.01); *C07K 7/08* (2013.01)

(58) Field of Classification Search
CPC ...................................................... C07K 14/00
See application file for complete search history.

(56) References Cited

FOREIGN PATENT DOCUMENTS

WO    WO 2012158169 A1 * 11/2012 ............. A61K 38/08

OTHER PUBLICATIONS

Sullivan, P.S., Chan, J.B., Levin, M.R., and Rao, J., Urine cytology and adjunct markers for detection and surveillance of bladder cancer. Am J Transl Res, 2010. 2(4): p. 412-40
Danuta B. Wronska, Magdalena Krajewska, Natalia Lygina, Juhua C. Morrison, Dalia Juzumiene, W. David Culp, Shrikumar A. Nair, Martyn Darby, and Christopher M. Hofmann, "Peptide-conjugated glass slides for selective capture and purification of diagnostic cells: Applications in urine cytology," BioTechniques.com, Aug. 2014: vol. 57, No. 2.

* cited by examiner

*Primary Examiner* — Bin Shen
(74) *Attorney, Agent, or Firm* — NK Patent Law, PLLC

(57) ABSTRACT

Cell binding peptides are provided for binding to cells including urothelial and thyroid follicular cells. The peptides are useful for detection and diagnosis of cancer including bladder and thyroid cancer. A device and method for using the device for capturing cells is provided, the device includes a support having attached cell binding peptide. The support can be a slide and the device can be used for detection and diagnosis of cancer including bladder and thyroid cancer. A kit is provided with instructions for capturing cells and a support with attached cell binding peptide for detection and diagnosis of bladder and thyroid cancer.

15 Claims, 11 Drawing Sheets

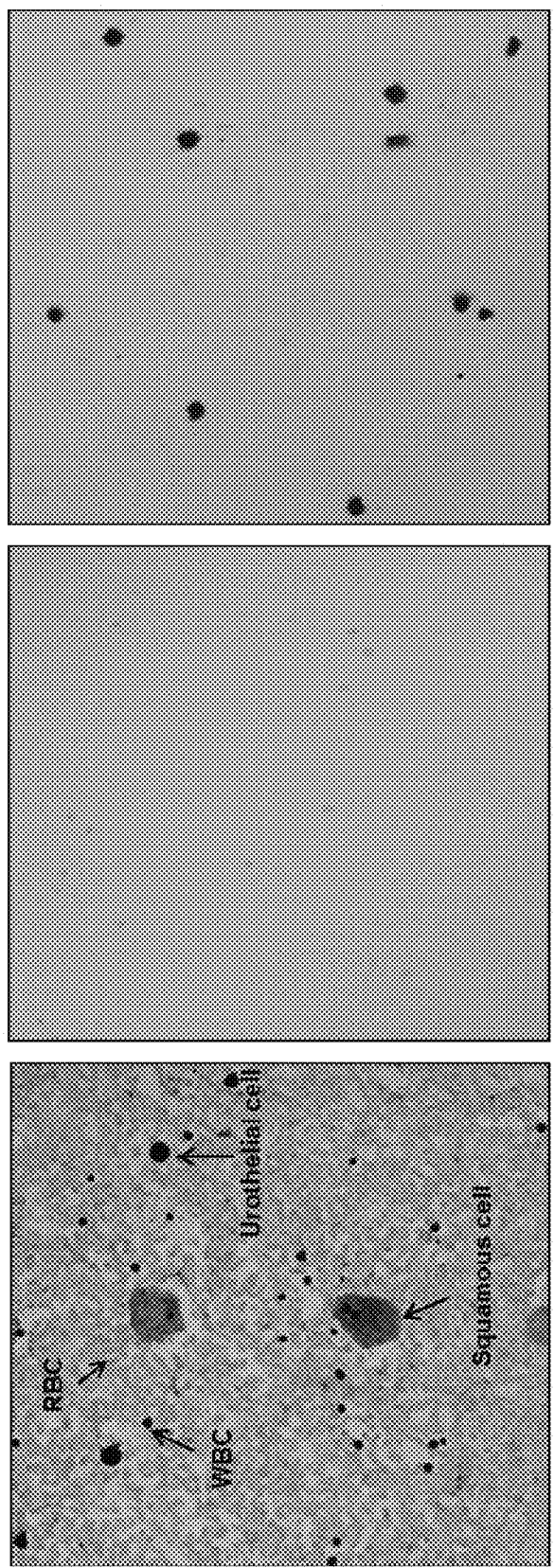

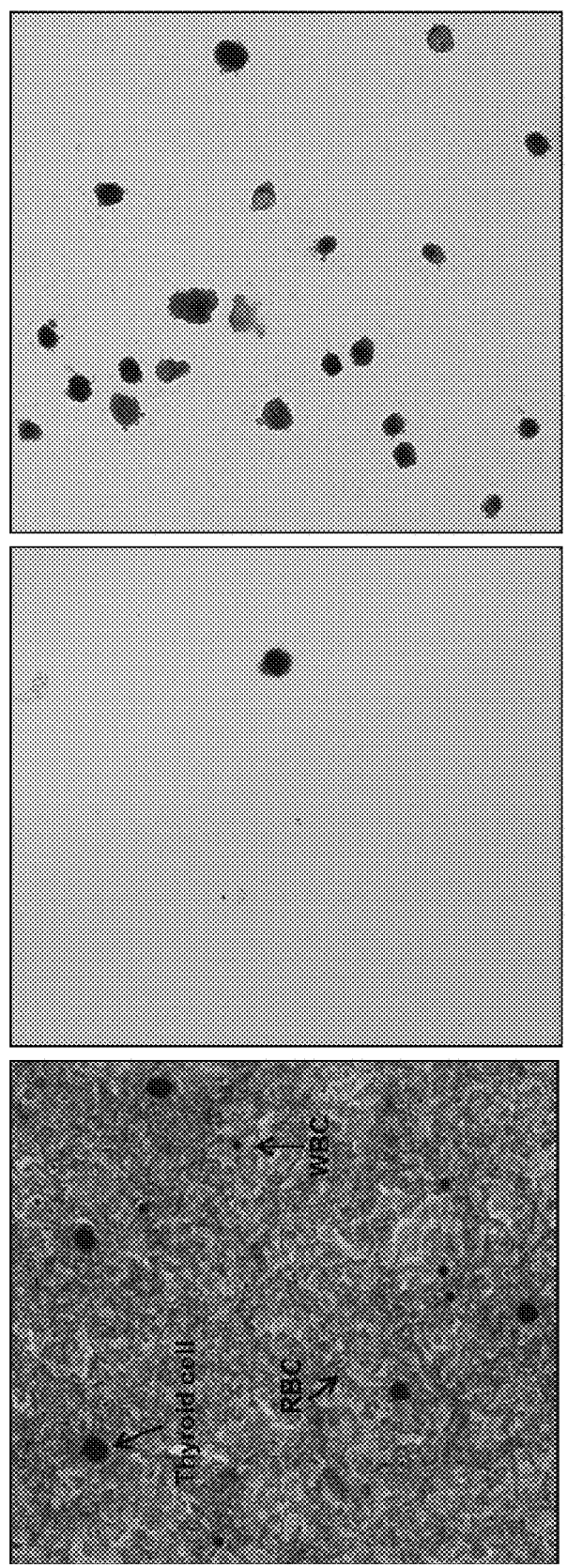

CELL BINDING PEPTIDES FOR DIAGNOSIS AND DETECTION

CROSS-REFERENCE TO RELATED APPLICATIONS

This application claims the benefit of U.S. Provisional Application No. 61/895,889 filed Oct. 25, 2013, which is hereby incorporated in its entirety by reference herein.

STATEMENT OF GOVERNMENT SUPPORT

This invention was made with U.S. Government support under the National Institutes of Health grant No.'s 2R44AR054229, 2R44GM077753, and 1R43DE022487. The U.S. Government has certain rights in the invention.

TECHNICAL FIELD

The present disclosure relates to the use of cell binding peptides for diagnosis and detection. More specifically, the present disclosure relates to the use of cell binding peptides for the detection and diagnosis of cancer.

BACKGROUND

Urine cytology is a non-invasive diagnostic method for detecting and monitoring bladder cancer, based on the collection of voided urine to examine exfoliated epithelial cells on glass slides. Follow-up tests, such as immunocytochemistry (ICC) and fluorescence in-situ hybridization (FISH), are also carried out using standard glass slides. However, hematuria is one of the most common presenting symptoms with bladder cancer, and both cytology and slide-based diagnostic testing can be confounded by the presence of red blood cells and inflammatory cells. Cytology slides prepared from specimens containing a high concentration of obscuring blood cells often lead to non-diagnostic results that necessitate repeat testing, unnecessary cystoscopy, and in some cases, exploratory biopsies. In all cases, these unnecessary procedures place a significant financial burden on both the patient and the healthcare facility. Although methods are available for processing specimens to concentrate urothelial cells and remove obscuring cell types, these methods are expensive, time-consuming, disruptive to cell phenotype, or all of the above.

Fine-needle aspiration (FNA) cytology is the standard technique for evaluating thyroid nodules. Hemorrhaging is common during the procedure, however, leading to an aspirate that is diluted by blood. Subsequent slide preparations are often suboptimal, resulting in nondiagnostic outcomes that necessitate additional testing or diagnostic surgery. In fact, quality is so unpredictable that a pathologist must often be present in the operating room to certify that the slides are adequate, thus adding substantial cost and complexity to the procedure. Furthermore, even with an optimal slide preparation, cytology yields indeterminate results up to 30% of the time. In the absence of a conclusive diagnosis, most indeterminate patients are guided towards an often unnecessary partial or near-total thyroidectomy. Immunocytochemistry and fluorescence in-situ hybridization are useful tools for diagnosing indeterminate cases, but such tests are not usually carried out on existing smears due to a paucity of follicular cells and an abundance of red blood cells. As a result, additional slides must be prepared using expensive and time-consuming techniques. Thus, there is a significant need for increasing the capture and isolation of follicular cells on FNA slide preparations, in addition to facilitating the development of ancillary diagnostic tests for categorizing indeterminate results.

The presently disclosed subject matter provides compositions and methods to address the above described needs and limitations of current healthcare practices.

SUMMARY OF THE INVENTION

In one embodiment, a cell binding peptide is provided comprising a sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; a conservatively substituted variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; or a variant having at least 70% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In one embodiment, a device is provided for capturing cells, the device including a support having an attached cell binding peptide for binding to and capturing cells, wherein the peptide includes a sequence as set forth in: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; a conservatively substituted variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; or a variant having at least 70% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In one embodiment, a method for capturing cells is provided, the method comprising: contacting a sample from a subject that comprises cells with the device having the support with attached cell binding peptide to bind to and capture cells, wherein the contacting is performed under conditions such that the cells are captured onto the support through binding to the cell binding peptide.

In one embodiment, a kit is provided for capturing cells for cytological evaluation, the kit including instructions for conducting capture of cells from a sample from a subject for cytological evaluation; and a support having an attached cell binding peptide for binding to and capturing the cells, wherein the peptide comprises a sequence as set forth in: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; a conservatively substituted variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; or a variant having at least 70% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

BRIEF DESCRIPTION OF THE DRAWINGS

The foregoing summary, as well as the following detailed description of various embodiments, is better understood when read in conjunction with the appended figures. For the purposes of illustration, there is shown in the Figures exemplary embodiments; however, the presently disclosed subject matter is not limited to the specific methods and exemplary embodiments disclosed.

FIGS. 8A-8C are images showing selective capture of exogenous urothelial cancer cells from voided urine spiked with whole blood with cell binding peptide SEQ ID NO: 5 according to embodiments of the present disclosure. A) Cells applied to a slide without peptide, slide not washed. B) Cells applied to a slide without peptide, slide washed. C) Cells applied to a slide coated with peptide SEQ ID NO: 5, slide washed. H&E staining, 100× magnification.

FIGS. 10A-10C are images showing selective capture of thyroid cancer cells from a mixture of thyroid cancer cells and whole blood with cell binding peptide SEQ ID NO: 3 according to embodiments of the present disclosure. A) Cells applied to a slide without peptide, slide not washed. B) Cells applied to a slide without peptide, slide washed. C) Cells applied to a slide coated with peptide SEQ ID NO: 3, slide washed. H&E staining, 200× magnification.

DETAILED DESCRIPTION OF THE INVENTION

Figure 1:
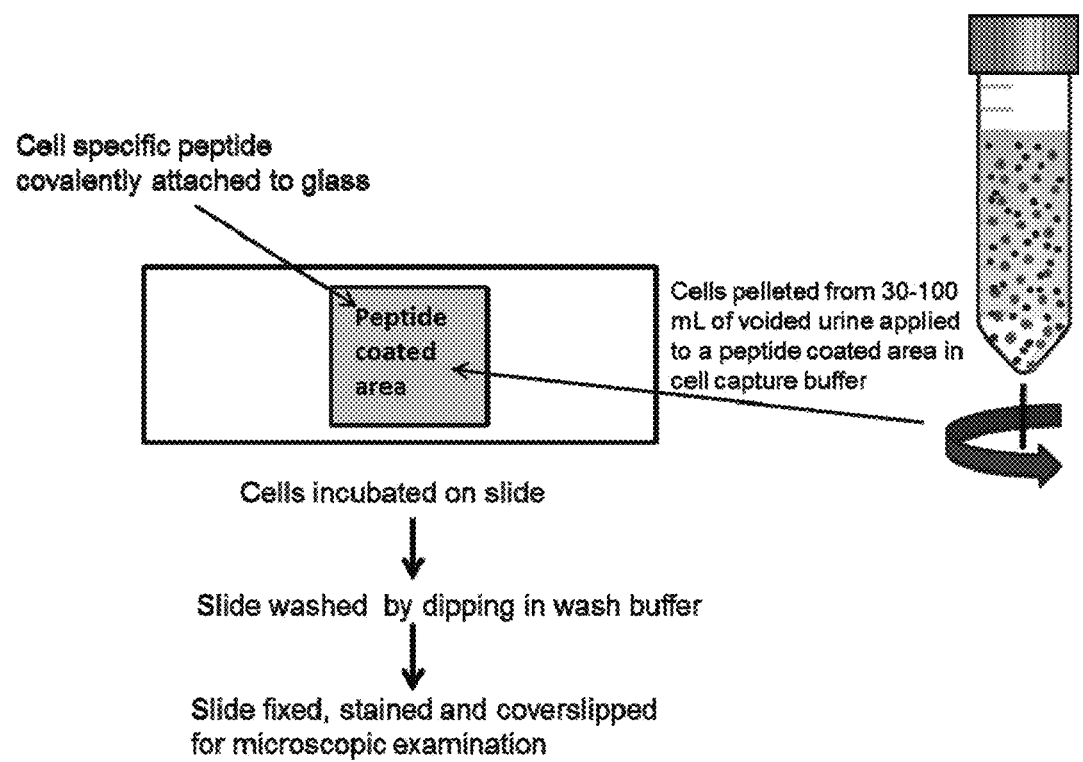
FIG. 1 is a flow diagram showing a method for capturing primary urothelial cells on a peptide coated glass slide according to embodiments of the present disclosure.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

The presently described subject provides compositions, methods, devices, and kits to address current limitations in processing specimens for detection and diagnosis of cancer, including bladder and thyroid cancer.

In one aspect, the present disclosure provides a more efficient and effective method to capture urothelial cells on diagnostic slides while removing unwanted cell types. Cell binding peptides are provided herein that can bind selectively to urothelial cells but not to red blood cells or inflammatory cells. In one embodiment, the cell binding peptides are attached to a slide to provide a simple and robust method for capturing urothelial cells from a mixed population. The slides can enable obscuring blood cells to be washed away from an area of interest on the slide. Washing the unbound cells (i.e. cells not bound to the cell binding peptides) can include moving the unbound cells from one area on the slide to another area on the slide such that the cells of interest are no longer obscured, but all the cells can be retained for analysis.

In one aspect, the present disclosure provides improved compositions and methods for evaluation of thyroid nodules. Fine-needle aspiration (FNA) cytology is the standard technique for evaluating thyroid nodules. There remains a significant need for improved compositions and methods for capture and isolation of follicular cells on FNA slide preparations. Cell binding peptides are provided herein that can bind selectively to follicular thyroid cells but not to red blood cells or white blood cells. In one embodiment, the cell binding peptides are attached to a slide to provide a simple and robust method for capturing follicular thyroid cells from a mixed population. The slides can enable obscuring blood cells to be washed away.

Articles "a" and "an" are used herein to refer to one or to more than one (i.e. at least one) of the grammatical object of the article. By way of example, "a cell" means at least one cell and can include a number of cells.

Unless otherwise defined, all technical terms used herein have the same meaning as commonly understood by one of ordinary skill in the art to which this disclosure belongs.

The term "cell binding peptide" is used herein, for the purposes of the specification and claims, to refer to an amino acid chain comprising a peptide that can bind to a cell. Cell binding peptides SEQ ID NOs: 1-10 are shown below in Table 1.

TABLE 1

Cell Binding Peptides

| SEQ ID NO: | Amino acid sequence (single letter code) |
|---|---|
| 1 | SSFSNYDSPWGPNWSVISR |
| 2 | SSIEDLPKDWPLFGWMSSR |
| 3 | SSLESVKEPWGPGWIPVSR |

TABLE 1-continued

Cell Binding Peptides

| SEQ ID NO: | Amino acid sequence (single letter code) |
|---|---|
| 4 | SSFGSD<u>CSPWGC</u>EWVPVSR |
| 5 | SSVALSFQAVPYDFHSSR |
| 6 | SSVQHAYQAWPGLGAYTSR |
| 7 | SSLFVAYPDSHRVWNVSR |
| 8 | SSFIEESFQLLRGLHQSR |
| 9 | SSFNSDSWLWAYSLQAESR |
| 10 | SFCPSNHDCIDWFIRSR |

In one embodiment, the cell binding peptide can bind to a urothelial cell. In one embodiment, the cell binding peptide can bind to a thyroid follicular cell. The cell binding peptides of the presently disclosed subject matter can include naturally occurring amino acids, synthetic amino acids, genetically encoded amino acids, non-genetically encoded amino acids, and combinations thereof; however, an antibody is specifically excluded from the scope and definition of a binding peptide of the presently disclosed subject matter. A binding peptide used in accordance with the presently disclosed subject matter can be produced by chemical synthesis, recombinant expression, biochemical or enzymatic fragmentation of a larger molecule, chemical cleavage of larger molecule, a combination of the foregoing or, in general, made by any other method in the art, and preferably isolated.

Cell binding peptides useful in the presently disclosed subject matter also include peptides having one or more substitutions, additions, and/or deletions of residues relative to the sequence of an exemplary cell binding peptide or growth factor binding peptide shown herein at Table 1. Thus, the binding peptides include those that differ from the exemplary sequences by about 1, 2, 3, 4, 5, 6, 7, or 8 amino acids, and include binding peptides that share sequence identity with the exemplary peptide of at least 65%, 66%, 67%, 68%, 69%, 70%, 71%, 72%, 73%, 74%, 75%, 80%, 81%, 82%, 83%, 84%, 85%, 86%, 87%, 88%, 89%, 90%, 91%, 92%, 93%, 94%, 95%, 96%, 97%, 98%, 99%, or greater sequence identity. Sequence identity can be calculated manually or it can be calculated using a computer implementation of a mathematical algorithm, for example, GAP, BESTFIT, BLAST, FASTA, and TFASTA, or other programs or methods known in the art. Alignments using these programs can be performed using the default parameters. A cell binding peptide can have an amino acid sequence consisting essentially of a sequence of an exemplary binding peptide or a cell binding peptide can have one or more different amino acid residues as a result of substituting an amino acid residue in the sequence of the exemplary binding peptide with a functionally similar amino acid residue (a "conservative substitution"), and thus the cell binding peptide containing the conservative substitution can substantially retain the binding activity of the exemplary binding peptide such that the variant retains cell binding activity. Examples of conservative substitutions include the substitution of one non-polar (hydrophobic) residue such as alanine, isoleucine, valine, leucine, or methionine for another; the substitution between asparagine and glutamine, the substitution of one large aromatic residue such as tryptophan, tyrosine, or phenylalanine for another; the substitution of one small polar (hydrophilic) residue for another such as between glycine, threonine, serine, and proline; the substitution of one basic residue such as lysine, arginine, or histidine for another; or the substitution of one acidic residue such as aspartic acid or glutamic acid for another.

Accordingly, cell binding peptides useful in the presently disclosed subject matter can include those peptides that are conservatively substituted variants of the binding peptides set forth in SEQ ID NOs: 1-10 and those peptides that are variants having at least 70% sequence identity or greater to the binding peptides set forth in SEQ ID NOs: 1-10. The variant cell binding peptides useful in the presently disclosed subject matter can retain the ability to bind to their target cells.

A cell binding peptide is provided comprising a sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; a conservatively substituted variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; or a variant having at least 70% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. The variant cell binding peptides can retain the ability to bind the cells. The cell binding peptide can comprise at most a total of 25, 30, 35, 40, 45, 50, 55, 60, 65, or 70 or more amino acids. The cell binding peptide can comprise at most a total of 40 amino acids. The cell binding peptide can comprise a sequence as set forth in SEQ ID NO's: 1-10, a conservatively substituted variant of SEQ ID NO's: 1-10, or a variant having at least 70% sequence identity to SEQ ID NO's: 1-10 having an additional 1, 2, 3, 4, 5, 6, 7, 8, 9, 10, 11, 12, 13, 14, 15, 16, 17, 18, 19, 20, 21, 22, or 23 or more amino acids at either or both the amino- or carboxyl-terminal end of the sequence such that the cell binding peptide can comprise the total of 25, 30, 35, 40, 45, 50, 55, 60, 65, or 70 or more amino acids.

Binding peptides can include L-form amino acids, D-form amino acids, or a combination thereof. Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; ornithine; and 3-(3,4-dihydroxyphenyl)-L-alanine ("DOPA"). Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

Further, a cell binding peptide according to the presently disclosed subject matter can include one or more modifications, such as by addition of chemical moieties, or substitutions, insertions, and deletions of amino acids, where such modifications provide for certain advantages in its use, such as to facilitate attachment to the support with or without a spacer or to improve peptide stability. The term "spacer" is used herein, for the purposes of the specification and claims, to refer to a compound or a chemical moiety that is optionally inserted between a cell binding peptide and the support. In some embodiments, the spacer also serves the function of a linker (i.e. to attach the binding peptide to the support). Therefore, the terms "linker" and "spacer" can be used interchangeably herein, for the purposes of the specification and claims, when performing the dual functions of linking (attaching) the peptide to the support and spacing the binding peptide from the support. In some cases the spacer can serve to position the binding peptide at a distance and in a spatial position suitable for binding and capture and/or in some cases the spacer can serve to increase the solubility of the binding peptide. Spacers can increase flexibility and accessibility of the binding peptide to its target, as well as increase the binding peptide density on the support surface. Virtually all chemical compounds, moieties, or groups suitable for such a function can be used as a spacer unless adversely affecting the binding behavior to such an extent that binding of the target to the binding peptides is prevented or substantially impaired. Thus, the term "cell binding peptide" encompasses any of a variety of forms of cell binding peptide modifications including, for example, amides, conjugates with proteins, conjugates with polyethylene glycol or other polymers, cyclic peptides, polymerized peptides, peptides having one or more amino acid side chain group protected with a protecting group, and peptides having a lysine side chain group protected with a protecting group. Any cell binding peptide derivative that has substantially retained target binding characteristics can be used in the practice of the presently disclosed subject matter.

The term "support" is used, for the purposes of the specification and claims, to refer to any material that is biologically compatible with cells and to which a cell binding peptide can be attached for the purpose of capturing the cells onto the support. A single cell binding peptide comprising SEQ ID NO: 1-10 can be attached to the support or combinations of 2, 3, or 4 or more of the cell binding peptides can be attached to the support.

A support of the presently disclosed subject comprises one or more materials including, but not limited to, one or more materials selected from: glass, metal, plastic, synthetic matrix, silica gel, polymer, or derivatives or combinations thereof. The support can be in the form of slides, beads, magnetic beads, microtiter plates, cell culture plates, mesh, fibrous form, hollow fibers, or sheets.

The term "attached" in reference to a cell binding peptide of the presently disclosed subject matter being "attached" to a support means, for the purposes of the specification and claims, a binding peptide being immobilized on the support by any means that will enable capture of the cell binding peptide target cell onto the support. A cell binding peptide can be attached to a support by any one of covalent bonding, non-covalent bonding including, one or more of hydrophobic interactions, Van der Waals forces, hydrogen bonds, ionic bonds, magnetic force, or avidin-, streptavidin-, and Neutravidin-biotin bonding.

Further, a chemical group can be added to the N-terminal amino acid of a cell binding peptide to block chemical reactivity of the amino terminus of the peptide. Such N-terminal groups for protecting the amino terminus of a peptide are well known in the art, and include, but are not limited to, lower alkanoyl groups, acyl groups, sulfonyl groups, and carbamate forming groups. Preferred N-terminal groups can include acetyl, 9-fluorenylmethoxycarbonyl (Fmoc), and t-butoxy carbonyl (Boc). A chemical group can be added to the C-terminal amino acid of a synthetic binding peptide to block chemical reactivity of the carboxy terminus of the peptide. Such C-terminal groups for protecting the carboxy terminus of a peptide are well known in the art, and include, but are not limited to, an ester or amide group. Terminal modifications of a peptide are often useful to reduce susceptibility by protease digestion, and to therefore prolong a half-life of a binding peptide in the presence of biological fluids where proteases can be present. In addition, as used herein, the term "cell binding peptide" also encompasses a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), an N-modified bond (—NRCO), and a thiopeptide bond (CS—NH).

In one embodiment, the cell binding peptides are covalently attached to a support. In one embodiment the binding peptides are covalently attached to a polymer comprised in the support. In one embodiment, the linkers/spacers for use in attaching binding peptides to supports have at least two chemically active groups (functional groups), of which one group binds to the support, and a second functional group binds to the binding peptide or in some cases it binds to the "spacer" already attached to the binding peptide. Preferably, the attachment of the binding peptides to the support is effected through a spacer. Virtually all chemical compounds, moieties, or groups suitable for such a function can be used as a spacer unless adversely affecting the peptide binding behavior to such an extent that binding of the target to the binding peptides is prevented or substantially impaired.

Again, the terms "linker" and "spacer" can be used interchangeably herein, for the purposes of the specification and claims, when performing the dual functions of linking (attaching) the binding peptide to the support and spacing the peptide from the support. In many embodiments herein, the linkers used to attach the binding peptide to the support function as both a linker and a spacer. For example, a linker molecule can have a linking functional group on either end while the central portion of the molecule functions as a spacer. The binding peptides of the presently disclosed subject matter can comprise a functional group that is intrinsic to the binding peptide (e.g., amino groups on lysine), or the functional group can be introduced into the binding peptide by chemical modification to facilitate covalent attachment of the binding peptide to the support. Similarly, the support can comprise a functional group that is intrinsic to the support or the support can be modified with a functional group to facilitate covalent attachment to the binding peptide. The binding peptide can be covalently attached to the support with or without one or more spacer molecules.

For example, linkers/spacers are known to those skilled in the art to include, but are not limited to, chemical compounds (e.g., chemical chains, compounds, reagents, and the like). The linkers/spacers may include, but are not limited to, homo-bifunctional linkers/spacers and heterobifunctional linkers/spacers. Heterobifunctional linkers/spacers, well known to those skilled in the art, contain one end having a first reactive functionality (or chemical moiety) to specifically link a first molecule (e.g, support), and an opposite end having a second reactive functionality to specifically link to a second molecule (e.g, cell binding peptide). It is evident to those skilled in the art that a variety of bifunctional or polyfunctional reagents, both homo- and hetero-functional can be employed as a linker/spacer with respect to the presently disclosed subject matter such as, for example, those described in the catalog of the PIERCE CHEMICAL CO., Rockford, Ill.; amino acid linkers/spacers that are typically a short peptide of between 3 and 15 amino acids and often containing amino acids such as glycine, and/or serine; and wide variety of polymers including, for example, polyethylene glycol. In one embodiment, representative linkers/spacers comprise multiple reactive sites (e.g., polylysines, polyornithines, polycysteines, polyglutamic acid and polyaspartic acid) or comprise substantially inert peptide spacers (e.g., polyglycine, polyserine, polyproline, polyalanine, and other oligopeptides comprising alanyl, serinyl, prolinyl, or glycinyl amino acid residues). In one embodiment, representative spacers between the reactive end groups in the linkers include, by non-limiting example, the following functional groups: aliphatic, alkene, alkyne, ether, thioether, amine, amide, ester, disulfide, sulfone, and carbamate, and combinations thereof. The length of the spacer can range from about 1 atom to 200 atoms or more. In one embodiment, linkers/spacers comprise a combination of one or more amino acids and another type of spacer or linker such as, for example, a polymeric spacer.

Suitable polymeric spacers/linkers are known in the art, and can comprise a synthetic polymer or a natural polymer. Representative synthetic polymer linkers/spacers include but are not limited to polyethers (e.g., poly(ethylene glycol) ("PEG"), 11 unit polyethylene glycol ("PEG10"), or 1 unit polyethylene glycol ("mini-PEG" or "MP"), poly(propylene glycol), poly(butylene glycol), polyesters (e.g., polylactic acid (PLA) and polyglycolic acid (PGA)), polyamines, polyamides (e.g., nylon), polyurethanes, polymethacrylates (e.g., polymethylmethacrylate; PMMA), polyacrylic acids, polystyrenes, and polyhexanoic acid, and combinations thereof. Polymeric spacers/linkers can comprise a diblock polymer, a multi-block copolymer, a comb polymer, a star polymer, a dendritic or branched polymer, a hybrid linear-dendritic polymer, a branched chain comprised of lysine, or a random copolymer. A spacer/linker can also comprise a mercapto(amido)carboxylic acid, an acrylamidocarboxylic acid, an acrlyamido-amidotriethylene glycolic acid, 7-aminobenzoic acid, and derivatives thereof.

In one embodiment, the binding peptide comprises one or more modifications to the peptide N-terminus, peptide C-terminus, or within the peptide amino acid sequence, to facilitate covalent attachment of the binding peptide to a support with or without a spacer. The binding peptides can comprise one or more modifications including, but not limited to, addition of one or more groups such as hydroxyl, thiol, carbonyl, carboxyl, ester, carbamate, hydrazide, hydrazine, isocyanate, isothiocyanate, amino, alkene, dienes, maleimide, α,β-unsaturated carbonyl, alkyl halide, azide, epoxide, N-hydroxysuccinimide (NHS) ester, lysine, or cysteine. In addition, a binding peptide can comprise one or more amino acids that have been modified to contain one or more chemical groups (e.g., reactive functionalities such as fluorine, bromine, or iodine) to facilitate linking the binding peptide to a spacer molecule or to the support to which the binding peptide will be attached.

The binding peptides can be covalently attached to the support through one or more anchoring (or linking) groups on the support and the binding peptide. The binding peptides of the presently disclosed subject matter can comprise a functional group that is intrinsic to the binding peptide, or the binding peptide can be modified with a functional group to facilitate covalent attachment to the support with or without a spacer. Representative anchoring (or linking) groups include by non-limiting example hydroxyl, thiol, carbonyl, carboxyl, ester, carbamate, hydrazide, hydrazine, isocyanate, isothiocyanate, amino, alkene, dienes, maleimide, α,β-unsaturated carbonyl, alkyl halide, azide, epoxide, NHS ester, lysine, and cysteine groups on the surface of the support. The anchoring (or linking) groups can be intrinsic to the material of the support (e.g., amino groups on a collagen or on a polyamine-containing support) or the anchoring groups can be introduced into the support by chemical modification.

The cell binding peptide can comprise one or more modifications to the peptide N-terminus, peptide C-terminus, or within the peptide amino acid sequence, wherein the modification is one or more of acetyl group, aldehyde group, hydroxyl group, thiol group, amino group, amino acids, lysine, cysteine, glycine-serine-serine-glycine (GSSG; SEQ ID NO: 11), polymers, synthetic polymers, polyethers, poly(ethylene glycol) ("PEG"), an 11 unit polyethylene glycol ("PEG10"), and a 1 unit polyethylene glycol ("mini-PEG" or "MP"), and combinations thereof. The peptide C-terminus can include the modification PEG10 linked to lysine, mini-PEG linked to lysine, or GSSG (SEQ ID NO: 11) linked to cysteine. One or both of an amine group of the peptide N-terminus and an internal lysine amine group of the peptide can include the acetyl group modification. The peptide C-terminus can include one of the modification PEG10 linked to lysine, mini-PEG linked to lysine, GSSG (SEQ ID NO: 11) linked to lysine, or GSSG (SEQ ID NO: 11) linked to cysteine.

In one embodiment, a device is provided for capturing cells, the device including a support having an attached cell binding peptide for binding to and capturing cells, wherein the peptide includes a sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; a conservatively substituted variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; or a variant having at least 70% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. The variant cell binding peptide can retain the ability to bind to and capture the cells.

The support of the device can include glass, metal, plastic, synthetic matrix, silica gel, polymer, or derivatives, or combinations thereof. The support of the device can be in the form of slides, beads, magnetic beads, microtiter plates, cell culture plates, mesh, fibrous form, hollow fibers, or sheets.

The cell binding peptide of the device can include one or more modifications to the peptide N-terminus, peptide C-terminus, or within the peptide amino acid sequence, wherein the modification is one or more of acetyl group, aldehyde group, hydroxyl group, thiol group, amino group, amino acids, lysine, cysteine, glycine-serine-serine-glycine (GSSG; SEQ ID NO: 11), polymers, synthetic polymers, polyethers, poly(ethylene glycol) ("PEG"), an 11 unit polyethylene glycol ("PEG10"), and a 1 unit polyethylene glycol ("mini-PEG" or "MP"), and combinations thereof.

One or both of an amine group of the peptide N-terminus and an internal lysine amine group of the peptide of the device anc include the acetyl group modification. The peptide C-terminus of the device can include the modification PEG10 linked to lysine, mini-PEG linked to lysine, GSSG (SEQ ID NO: 11) linked to lysine, or GSSG (SEQ ID NO: 11) linked to cysteine.

The support of the device can be in the form of a slide. The slide of the device can be a N-Hydroxysuccinimide (NHS)-derivatized glass slide, and the cell binding peptide can be attached to the slide through a bond between a C-terminal lysine on the peptide and the NHS group on the slide. The slide of the device can be an epoxy-derivatized glass slide, and the cell binding peptide can be attached to the slide through a bond between a C-terminal cysteine on the peptide and the epoxy group on the slide.

The slide of the device can be for evaluation of the captured cells for one or both of bladder cancer and thyroid cancer.

The support of the device can be in the form of beads or magnetic beads and the captured cells can include circulating tumor cells.

In one embodiment, a method is provided for capturing cells, the method including contacting a sample from a subject that comprises cells with the device of the present disclosure having the support with attached cell binding peptide to bind to and capture cells, wherein the contacting is performed under conditions such that the cells are captured onto the support through binding to the cell binding peptide.

In the method, the sample can include, but is not limited to, blood, plasma, urine, or fine needle aspirate.

In the method, the cell binding peptide can bind to one or both of urothelial cells and thyroid follicular cells, and the captured cells can be for cytological evaluation for one or both of bladder cancer and thyroid cancer. The cell binding peptide can bind to the urothelial cells and thyroid follicular cells selectively over red blood cells (RBCs) and white blood cells (WBCs). In one embodiment of the method, the cancer is bladder cancer, the cell binding peptide can bind to urothelial cells, and the sample can include urine from the subject. In one embodiment of the method, the cancer is thyroid cancer, the cell binding peptide can bind to thyroid follicular cells, and the sample can include thyroid fine needle aspirate (FNA) from the subject.

In the method, the support can be in the form of slides, beads, magnetic beads, microtiter plates, cell culture plates, mesh, fibrous form, hollow fibers, or sheets. In the method, the support can be in the form of a slide. The support can include glass, metal, plastic, synthetic matrix, silica gel, or polymer, and derivatives and combinations thereof. The method can further include incubating the cells on the support. The method can further include washing the support such that the unbound cells are removed and the bound cells remain. Removing the unbound cells by washing can include moving the cells from one area on the support to another area on the support. In this manner the unbound cells can be retained for analysis, while still being removed from one or more areas of interest on the support. The wash can be performed by dipping the support in wash buffer. The support can be fixed, stained and coverslipped for microscopic examination. The support can be fixed and stained with antibodies for immunocytochemistry.

In the method, the contacting of the sample with the device can be performed by adsorption chromatography, adsorption filtration, sedimentation, or centrifugation, and combinations thereof.

In one embodiment of the method, the captured cells can include circulating tumor cells and the support can be in the form of beads or magnetic beads.

In one embodiment, a kit is provided for capturing cells for cytological evaluation, the kit including instructions for conducting capture of cells from a sample from a subject and a support having an attached cell binding peptide for binding to and capturing the cells. The peptide of the kit includes a sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; a conservatively substituted variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; or a variant having at least 70% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In the kit, the cell binding peptide can bind to one or both of urothelial cells and thyroid follicular cells, and the cytological evaluation can be for one or both of bladder cancer and thyroid cancer. The kit can further include reagents for capturing, washing, fixing, and staining the cells.

The kit can be for bladder cancer, the cell binding peptide can bind to urothelial cells, and the sample can include urine from the subject. The kit can be for thyroid cancer, the cell binding peptide can bind to thyroid follicular cells, and the sample can include thyroid fine needle aspirate (FNA) from the subject.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Generation of Synthetic Binding Peptides

Peptide Synthesis:

Binding peptide sequences were synthesized using standard Solid-Phase peptide synthesis techniques on a SYMPHONY Peptide Synthesizer (Protein Technologies, Inc., Tucson, Ariz.) using standard Fmoc/t-Bu chemistry with the following coupling reagents at a 1:1:1:2 ratio—Amino acids; O-(benzotriazol-1-yl)-N,N,N',N'-tetramethyluronium hexafluoroborate (HBTU); 1-hydroxybenzotriazole (HOBt); and N-Methylmorpholine (NMM). A 20% (v/v) solution of piperidine in DMF was utilized for Fmoc removal. Peptides were synthesized on Fmoc-NH-Rink-Ahx-MBHA resin or on Fmoc-PAL-Peg-PS resin yielding peptides with C-terminal amides.

Amino acids with orthogonal side-chain protecting groups were coupled in 5-fold excess in the synthesis cycles, and all residues were doubly or triply coupled for 1 h. The coupling reactions were monitored by Kaiser ninhydrin test or chloranil test. After all amino acid residues were coupled and following the peptide assembly, simultaneous cleavage off resin and side chain deprotection was achieved by treatment with a trifluoroacetic acid (TFA) cocktail. Crude peptide was precipitated with cold diethyl ether and purified by high-performance liquid chromatography on a WATERS Preparative/Semi-preparative HPLC system on a VYDAC C18 silica column (preparative 10 µm, 250 mm×22 mm) using a linear gradient of water/acetonitrile containing 0.1% TFA. Homogeneity of the synthetic peptides was evaluated by analytical RP-HPLC (VYDAC C18 silica column, 10 µm, 250 mm×4.6 mm). The fractions containing the desired product were lyophilized to give a white fluffy solid. The identity of the peptides were confirmed with electrospray ionization mass spectrometry (ESI-MS) on Waters ZQ4000 system. Biotinylated peptides were synthesized similarly, using Fmoc-K(Biotin) as a building block and with 'GSSG' (SEQ ID NO: 11) or other spacer group added to the C-terminus of the peptide.

Example 2

Peptide Cell Binding

Figure 2:
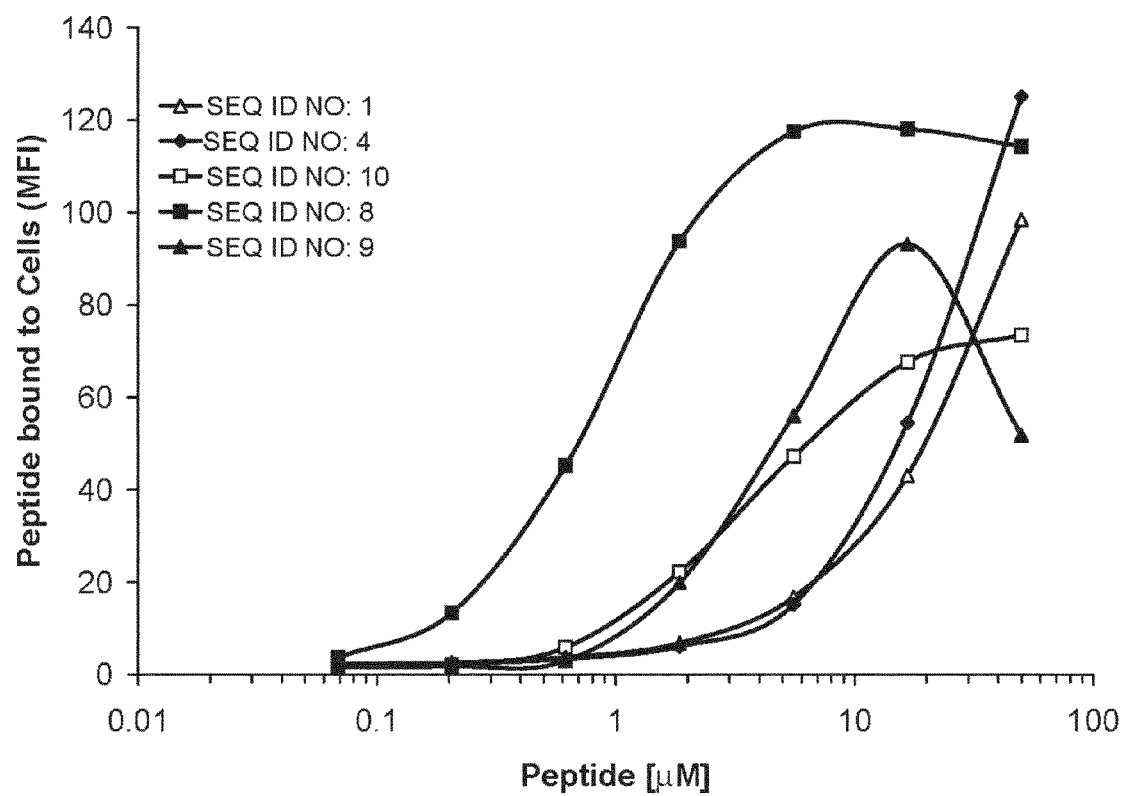
FIG. 2 is a graph showing peptide binding to J82 bladder cancer cells measured by fluorescence intensity in a flow cytometry assay according to embodiments of the present disclosure.

Synthetic biotinylated cell binding peptides were examined for their ability to bind to a bladder cancer cell line, J82 (ATCC, HTB1). The cell binding peptide was synthesized with a PEG-10 spacer and a carboxyl terminal lysine-biotin. J82 cells were grown to confluency on tissue-culture treated polystyrene. Cells were washed with PBS and released from the support with 0.05% trypsin. Trypsin was removed by centrifuging cells at 500×g and resuspending in PBS supplemented with 0.5% BSA and 2 mM EDTA to a concentration of 68,000 cells/ml. Aliquots of cells (50 µL) were separately incubated in 100 µl PBS/0.5% BSA/2 mM EDTA containing a final concentration of 0, 0.07, 0.21, 0.62, 1.85, 5.55, 16.7, and 50 µM peptide for 60 min at 4° C. Cells were then washed thrice in 1.8 ml PBS/0.5% BSA/2 mM EDTA with 500×g centrifugation for 5 min between washes. Approximately 50 µl of wash buffer remained with the cells after the final wash. Fluorescently-tagged neutravidin (Neutravidin-PE from INVITROGEN), 50 µl of a 5 µg/ml solution in PBS/0.5% BSA/2 mM EDTA was then added to the cells to label biotinylated peptide bound to cells. Neutravidin binding to biotinylated peptide was allowed to proceed for 30 min on ice. Cells were then washed with PBS/0.5% BSA/2 mM EDTA, and acquired on a BD FACSARRAY. Peptide reactivity was then measured as geometric mean of fluorescence intensity. The affinity of peptides for J82 bladder cancer cell line is shown in FIG. 2.

Example 3

Capture of Cultured J82 Tumor Cells from Urine with Cell Binding Peptide Attached to a Support To demonstrate the ability of cell binding peptides to recover tumor cells from urine, biotinylated peptides were immobilized on Streptavidin coated magnetic beads and used to separate tumor cells from white blood cells.

A green fluorescent leukocyte preparation was prepared as follows. Red blood cells in 2 ml anti-coagulated human blood were lysed by the addition of 30 ml of a hypotonic medium and incubation for 10 min at room temperature. Intact cells and debris were recovered by centrifugation at 300×g. Pelleted material was resuspended with PBS/0.5% BSA/2 mM EDTA and filtered through a 100 micron nylon filter. Leukocytes (3×10$^6$) were labeled with 5 µM Cell Tracker Green CMFDA (LIFE TECHNOLOGIES/MOLECULAR PROBES) in EMEM growth medium without serum for 45 min. Excess dye was removed by centrifugation at 500×g for 5 min and washing with PBS/0.5% BSA/2 mM EDTA and cells were exposed to 10% serum containing medium for 45 min to allow dye conversion.

Red fluorescent J82 cells were prepared as follows: An 80% confluent culture of J82 bladder cancer cells was labeled with 5 µM Cell Tracker Red CMPTX (LIFE SCIENCES/MOLECULAR PROBES) in EMEM growth medium without serum for 90 min. Excess dye was removed by washing the flask with EMEM/10% FBS and cells were exposed to 10% serum containing medium for 1.5 h for dye conversion. The cells were then washed with PBS and released from the flask with 0.05% trypsin. Cells were recovered and trypsin removed by centrifugation at 500×g followed by washing in PBS/0.5% BSA/2 mM EDTA.

Biotinylated peptides SEQ ID NO: 1 and SEQ ID NO: 10 were synthesized with a C-terminal Peg10 group attached to a lysine as described in Example 1. The biotinylated peptides were conjugated to magnetic microbeads (MILTENYI) by incubating 400 µl of bead suspension in 20 µM peptide for 30 min on ice with occasional mixing. Unbound peptide was removed by binding the beads to a Miltenyi MS column placed in a magnetic field. Beads were washed with PBS/0.5% BSA/2 mM EDTA and peptide conjugated beads released by removing the Miltenyi MS column from the magnetic field. A mixture of green fluorescent leukocytes and red fluorescent J82 bladder cancer cells was variously prepared in ratios between 12.5:1 and 20:1. The cell mixture (725,000 cells total) was added to 5 ml human urine and then 250 µl of peptide-magnetic bead conjugate. The whole was incubated for 45 min at room temperature with rotation.

Figure 3:
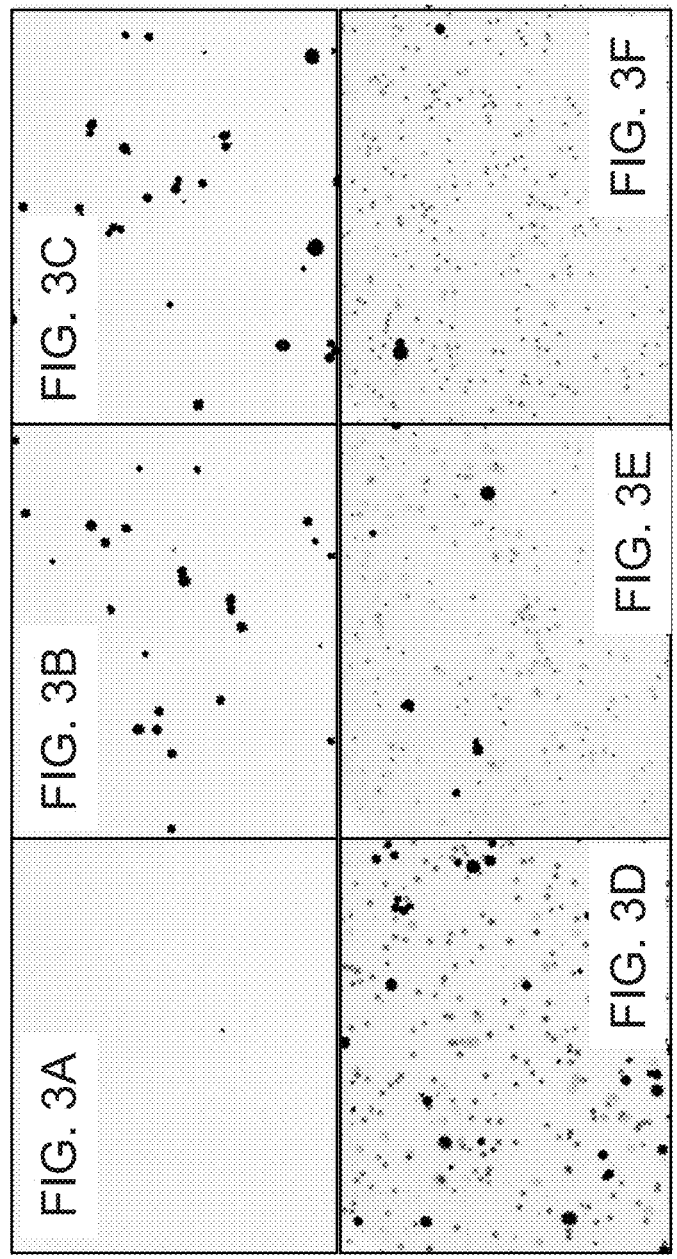
FIGS. 3A-3F are a set of images showing enrichment of fluorescently labeled J82 bladder cancer cells from leukocytes selectively captured from urine using cell binding peptides conjugated to magnetic beads according to embodiments of the present disclosure. Panels A-C show cells that were captured and Panels D-F show uncaptured cells. Panels A and D show cells in the absence of peptide, Panels B and E show cells using Peptide SEQ ID NO: 10, and Panels C and F show cells using Peptide SEQ ID NO: 1. The J82 bladder cancer cells are larger and shown in black. Blood leukocytes are smaller and shown in gray.

To capture cells the peptide-magnetic bead cell mixture was passed over a Miltenyi MS column pre-equilibrated with PBS/0.5% BSA/2 mM EDTA and held in a magnetic field. Unbound cells were washed out with PBS/0.5% BSA/2 mM EDTA and retained. Cells bound to the peptide-magnetic bead conjugate were released from the Miltenyi MS column by removing the column from the magnetic field. The peptide bound cells and the cells that did not bind to the column were visualized by indirect fluorescent microscopy and the ratio of J82 (red) to leukocytes (green) was determined. The data in FIG. 3 and Table 2 below show a 463-fold to 588-fold enrichment of J82 cells from leukocytes in urine. Enrichment is the fold change in the ratio of J82 cells:total leukocytes after capture divided by the ratio of J82 cells:total leukocytes before capture.

TABLE 2

| Peptide | J82 bladder tumor cells | Total Blood Leukocytes | Enrichment Factor |
|---|---|---|---|
| None | 0.89 | 0.08 | 11.4 |
| SEQ ID NO: 10 | 53.6 | 0.09 | 588 |
| SEQ ID NO: 1 | 48.2 | 0.1 | 463 |

Example 4

Method of Peptide Conjugation to Glass Using N-Hydroxysuccinimide (NHS)-Derivatization Peptides were synthesized in a conjugatable format for unidirectional conjugation to glass. Peptides were attached to glass through a covalent bond formed between the lysine on C-terminus of the peptide and an N-Hydroxysuccinimide (NHS) group on the glass. Briefly, microscope glass slides functionalized with NHS groups ((MICROSURFACES, Inc)) were incubated with peptide solution at 200 µM for 2 hours at 30° C., ~75% RH. At the end of the incubation the slides were washed 3 times for 5 min in washing buffer (1×PBS, 0.05% Tween 20) and subsequently deactivated in deactivation solution (MICROSURFACES, Inc) for 30 min at 30° C., ~75% RH to deactivate any remaining uncoupled NHS groups. Eventually slides were washed twice for 5 min in washing buffer prior to being blocked for 1 hour in blocking buffer (PBS, 0.5% BSA, 2 mM EDTA).

Example 5

Method of Peptide Conjugation to Glass Using Epoxy Functional Groups

Peptides SEQ ID NO: 6 and SEQ ID NO: 7 were synthesized with a GCCG linker followed by a cysteine on the C-terminus and conjugated through the cysteine SH group to glass slides with epoxy functional groups. Briefly, the glass slides were incubated with peptide solution at 200 μM for 2 hours at 30° C. At the end of the incubation the slides were washed 3 times for 5 min in wash buffer (1×PBS, 0.05% Tween 20) and subsequently deactivated in deactivation solution (50 mM Ethanolamine in 0.1M Tris buffer pH 9) for 30 min at 30° C. Eventually slides were washed twice for 5 min in wash buffer prior to being blocked for 1 hour in blocking buffer (PBS, 0.5% BSA, 2 mM EDTA).

Example 6

Cell Binding to Peptides Conjugated to Glass Slides

Microscope glass slides with discrete areas functionalized with peptide were used as diagnostic cell capture devices as shown in FIG. 1. Cells used were cultured cell lines established from human transitional bladder carcinomas (J82, ATCC HTB-1 and T24, ATCC HTB-4), cells isolated from voided urine of healthy donors (primary cells), a cultured cell line established from human thyroid carcinoma (SW579) or white blood cells (WBC) obtained from human whole blood by lysing red blood cells.

Cell suspension was prepared in cell capture buffer (PBS, 0.5% BSA, 2 mM EDTA, 0-200 mM glucose) and applied directly to a peptide functionalized slide in which peptide was attached to a glass slide using the N-Hydroxysuccinimide chemistry described in Example 4 with a pipetting device. The cells were incubated on the slide for 15 min and then drained by tipping the slide to the side. The slides were washed by dipping in wash buffer (PBS, 0.5% BSA, 2 mM EDTA) to wash away unbound cells. Slides were fixed in paraformaldehyde, dried, stained (H&E) and cover slipped for microscopic examination in a bright field. For fluorescent microscopy the cells were labeled with fluorescent dyes (CELLTRACKER Green or Red; LIFE TECHNOLOGIES, INC) prior to applying to the slide. Following the 15 min incubation the slides were washed, fixed, dried and mounted with a fluorescent mounting medium for microscopic examination in a dark field.

Figure 4:
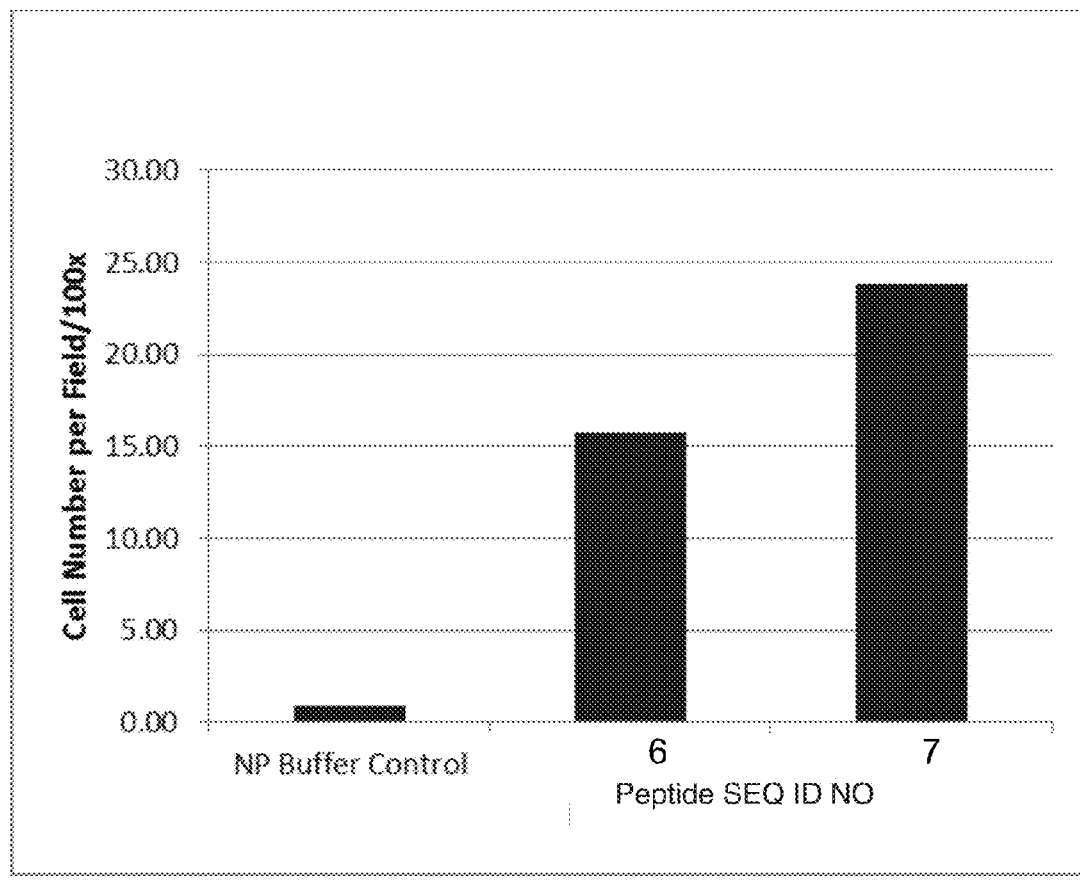
FIG. 4 is a graph showing binding of urothelial cancer cells, T24, to epoxy glass slide functionalized with cell binding peptides compared to a buffer control according to embodiments of the present disclosure.

In another experiment, urothelial cancer cells, T24, were prepared as cell suspension in capture buffer (PBS, 0.5% BSA, 2 mM EDTA, 0-200 mM glucose) and applied directly to a peptide functionalized slide in which peptide was attached to a glass slide using the epoxy chemistry described in Example 5 with a pipetting device. Cells were labeled with fluorescent dyes (CELLTRACKER Green; LIFE TECHNOLOGIES, INC) prior to applying to the slide. The cells were incubated on the slide for 15 min and then drained by tipping the slide to the side. The slides were washed by dipping in wash buffer (PBS, 0.5% BSA, 2 mM EDTA) to wash away unbound cells. Slides were fixed, dried and mounted with a fluorescent mounting medium for microscopic examination in a dark field. FIG. 4 shows binding of urothelial cancer cells, T24, to epoxy glass slide functionalized with peptide SEQ ID NO: 6 or SEQ ID NO: 7 synthesized with a C-terminal GSSG (SEQ ID NO: 11) spacer group and cysteine according to Example 1. Input peptide concentration was 200 μM. Captured cells were counted under a fluorescent microscope. Data are presented as cell number per microscope field at 100× magnification averaged from 8 fields. The Slide area not coated with peptide did not show cell capture (NP Buffer Control in FIG. 4).

Example 7

Urine Cytology

Selective capture of urothelial cells, J82, was achieved from a mixture of J82 and white blood cells (WBC) on a peptide coated glass slide using cell binding peptides of the present disclosure. In this Example, peptides were synthesized with a C-terminal Peg10 spacer followed by a lysine and conjugated to the glass slide according to Example 4.

Figure 5A:
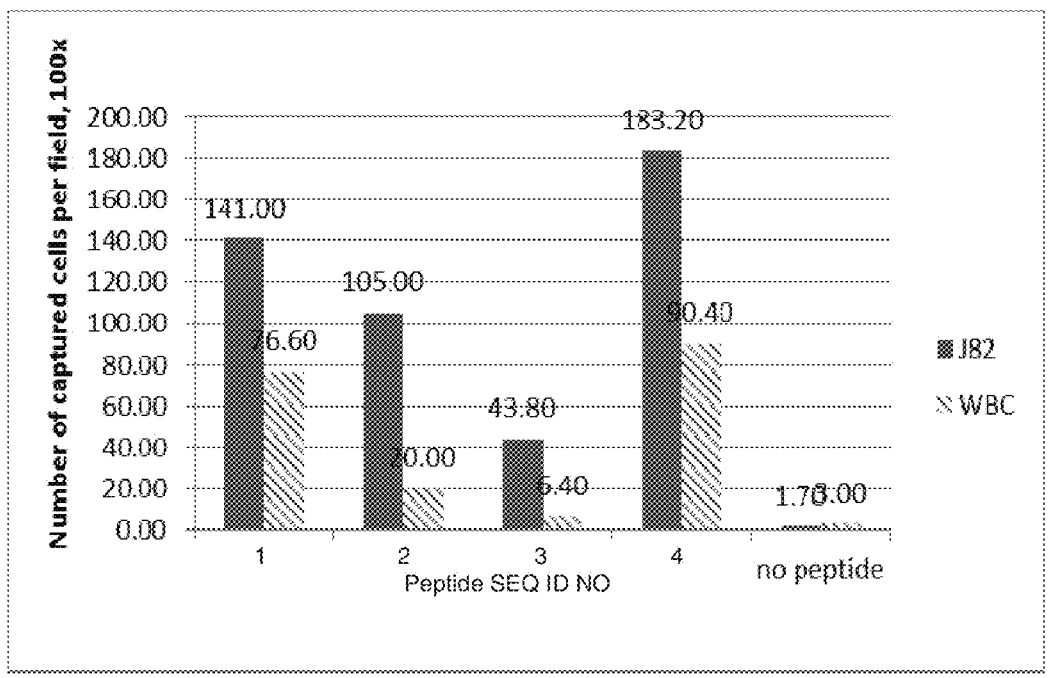
FIGS. 5A-5B are graphs showing selective capture of urothelial cells, J82, from a mixture of J82 and white blood cells (WBC) on a cell binding peptide-coated glass slide according to embodiments of the present disclosure. A) Graph showing the number of cells captured. B) Graph showing the change in WBC to J82 ratio.
Figure 5B:
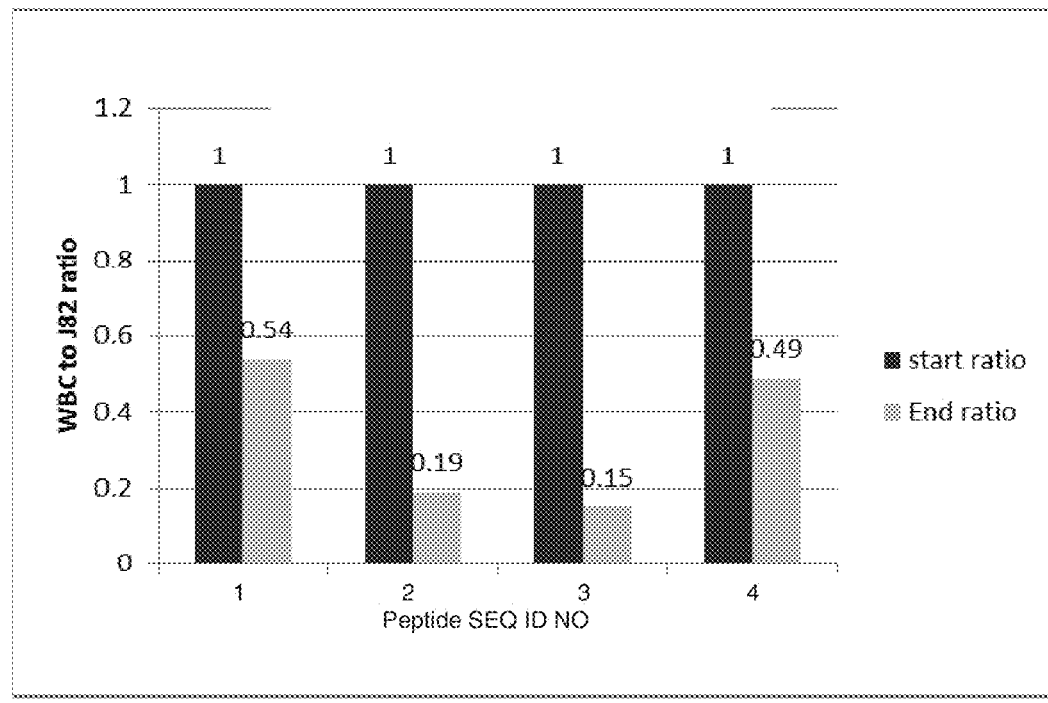

The cell binding peptides used in a first experiment were SEQ ID NO: 1, SEQ ID NO: 2, SEQ ID NO: 3, and SEQ ID NO: 4. Panel A of FIG. 5 shows absolute cell capture and panel B shows the change in cell ratio following cell capture on the slide. Human WBC and J82 cells were labeled with different CELLTRACKER dyes, mixed at a 1 to 1 ratio and applied to a slide with discrete areas coated with peptides. The slide was washed of unbound cells and captured cells were counted under a fluorescent microscope. Data are presented in FIGS. 5A & 5B as cell number per microscope field at 100× magnification averaged from 10 fields. The slide area not coated with peptide was used as a negative control. Preferential capture of J82 urothelial cells was observed leading to depletion of WBC up to 85%. Tested peptides differed in capture selectivity with SEQ ID NO: 3 and SEQ ID NO: 2 being more selective (lower WBC to J82 end ratio) than SEQ ID NO: 1 and SEQ ID NO: 4. Thus the degree of WBC removal from the diagnostic sample can be controlled by using a peptide most suitable for the application. For example, in some circumstances the presence of some WBCs on the slide may provide valuable clinical information.

Figure 6A:
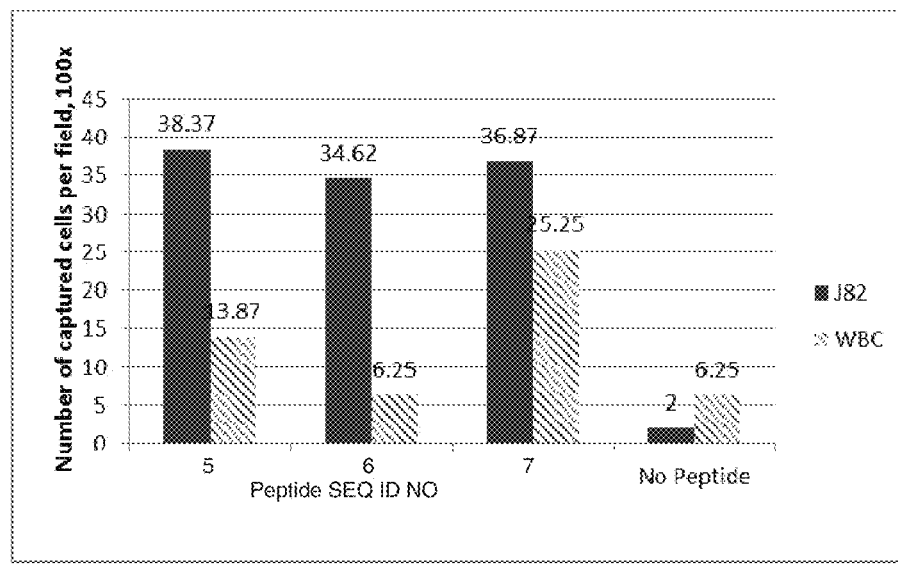
FIGS. 6A-6B are graphs showing selective capture of urothelial cells, J82, from a mixture of J82 and white blood cells (WBC) on a cell binding peptide coated glass slide according to embodiments of the present disclosure. A) Graph showing the number of cells captured. B) Graph showing the change in WBC to J82 ratio.
Figure 6B:
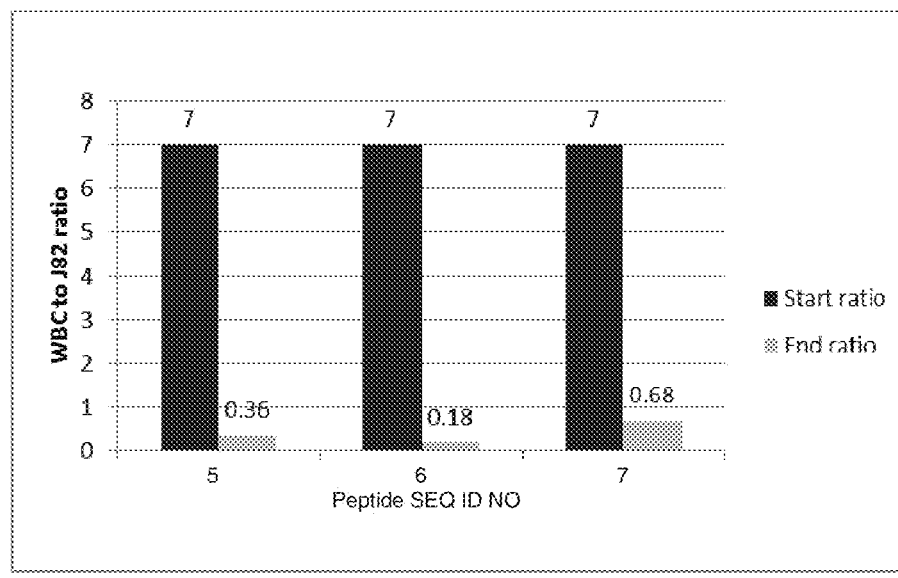
Figure 7:
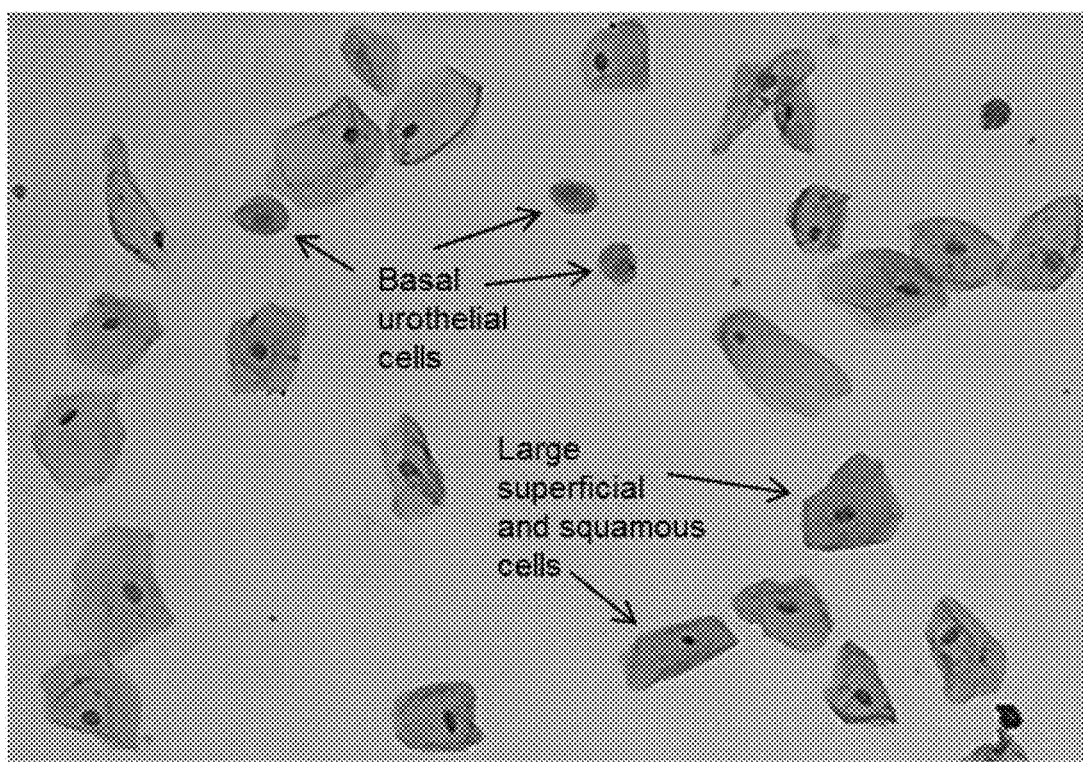
FIG. 7 is an image showing the types of primary cells isolated from voided urine. H&E staining, 100× magnification.

In another experiment, selective capture of urothelial cancer cells, J82, was achieved from a mixture of J82 and WBC on a peptide coated glass slide using peptides SEQ ID NO: 5, SEQ ID NO: 6, and SEQ ID NO: 7. Panel A of FIG. 6 shows absolute cell capture and panel B of FIG. 6 shows the change in cell ratio following cell capture on the slide. Human WBC and J82 cells were labeled with different CELLTRACKER dyes, mixed at 7 to 1 ratio and applied to a slide with discrete areas coated with peptides. The slide was washed of unbound cells and captured cells were counted under a fluorescent microscope. Data are presented as cell number per microscope field at 100× magnification averaged from 8 fields. The slide area not coated with peptide was used as a negative control. Preferential capture of J82 urothelial cells was observed leading to depletion of WBC up to 97%. Tested peptides differed in capture selectivity with SEQ ID NO: 6 and SEQ ID NO: 5 being more selective (lower WBC to J82 end ratio) than SEQ ID NO: 7.

In another experiment, primary cells from voided urine were selectively captured onto peptide coated glass slides. Specifically, cells were isolated from 40 mL of voided urine from a second morning void and applied to a glass slide with a discrete area coated with peptide. Cells were visualized by H&E staining and counted in a bright field. Results are presented in Table 3 below as a cell number per the entire peptide coated area (2.67 cm$^2$). Cells were classified into 2 categories: deep urothelial cells (basal and intermediate) and superficial urothelial (umbrella) and squamous cells. The sample adequacy criterion for urine cytology is at least 15 well visualized basal or intermediate cells[1]. Peptide selectivity is reflected in preferential capture of either the deep urothelial cells (peptides SEQ ID NO: 4 and SEQ ID NO: 5) or superficial and squamous cells (peptide SEQ ID NO: 6).

TABLE 3

| Peptide | Number of captured basal and intermediate cells/ peptide coated area | Number of captured superficial and squamous cells/peptide coated area |
| --- | --- | --- |
| SEQ ID NO: 4 | 21 | 6 |
| SEQ ID NO: 5 | 40 | 19 |
| SEQ ID NO: 6 | 5 | 35 |
| No peptide | 4 | 4 |

In another experiment urothelial cancer cells from voided urine were selectively captured using peptide SEQ ID NO: 5. Specifically, voided urine was spiked with whole blood to model hematuria, the most common presenting symptom of bladder cancer, and with J82 urothelial cancer cells. Cells were isolated from urine by centrifugation and applied to a slide coated with peptide SEQ ID NO: 5 or slides not coated with peptide. Panel A of FIG. 8 shows cells applied to a slide without peptide, slide not washed. Blood cells are retained on the slide obscuring diagnostic cells. Panel B of FIG. 8 shows cells applied to a slide without peptide, slide washed. All cells are washed away. Panel C of FIG. 8 shows cells applied to a slide coated with peptide SEQ ID NO: 5, slide washed. Blood cells are washed away and urothelial cells retained. H&E staining, 100× magnification.

In the following experiment, the sensitivity of the peptide coated slide was tested. In a clinical setting, urine specimens may contain significant numbers of blood cells that can obscure the urothelial cells of interest. To demonstrate the ability of the peptide coated slides to enrich for a scarce urothelial cell population from an overwhelming number of obscuring cells, J82 urothelial cells (100, 500, or 1000 cells) and WBCs were mixed in a 1:72 ratio and applied to wells on a slide modified with peptide SEQ ID NO: 2). Urothelial cells and WBCs were labeled with CELLTRACKER Red and Green, respectively. After a 15 min incubation on the slide, unbound cells were washed away, and bound cells were counted under a fluorescent microscope (N=2 wells; N=4 100× fields per well). There was a 7.6-fold reduction in WBCs relative to urothelial cells, corresponding to an 86% depletion of WBCs from the input material. This indicates that the peptide-coated slides can enrich for scarce urothelial cells out of a mixed population heavily dominated by obscuring cells, which can be critical for patients presenting with gross hematuria.

Example 8

Thyroid Cytology

Selective capture of thyroid cells, SW579 (ATCC HTB-107 from squamous cell carcinoma of the thyroid), was achieved from a mixture of SW579 and WBC on a peptide coated glass slide. In this Example, peptides were synthesized with a C-terminal Peg10 spacer followed by a lysine and conjugated to the glass slide using according to Example 4.

Figure 9A:
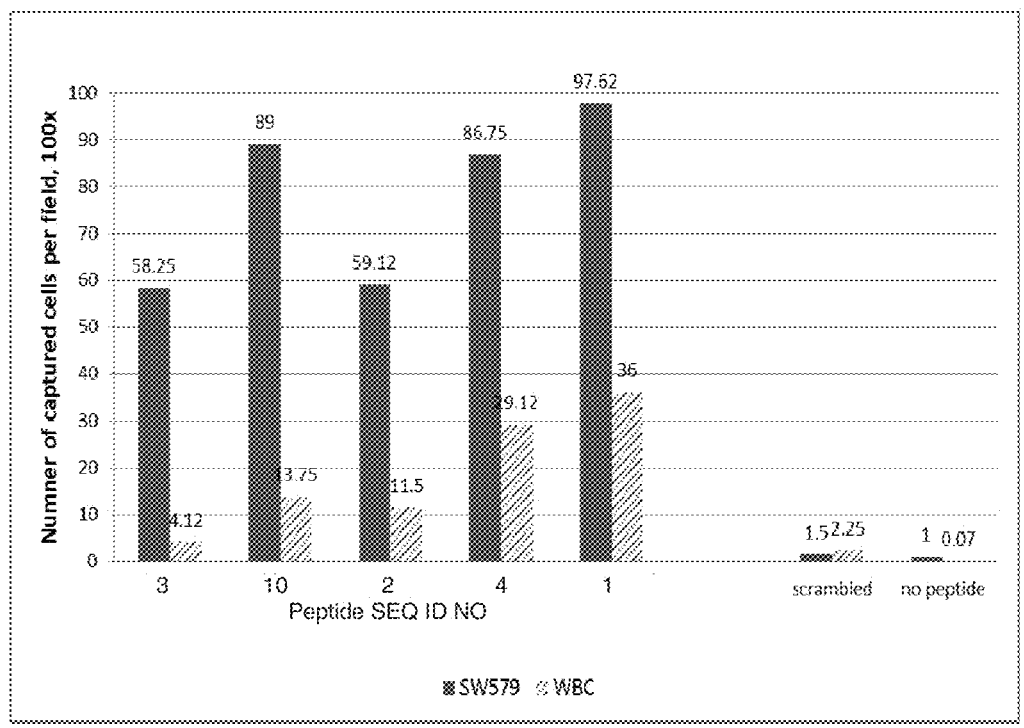
FIGS. 9A-9B are graphs showing selective capture of thyroid cells, SW579, from a mixture of SW579 and white blood cells (WBC) on a cell binding peptide-coated glass slide according to embodiments of the present disclosure. A) Shows the number of cells captured. B) Shows the change in WBC to SW579 ratio.
Figure 9B:
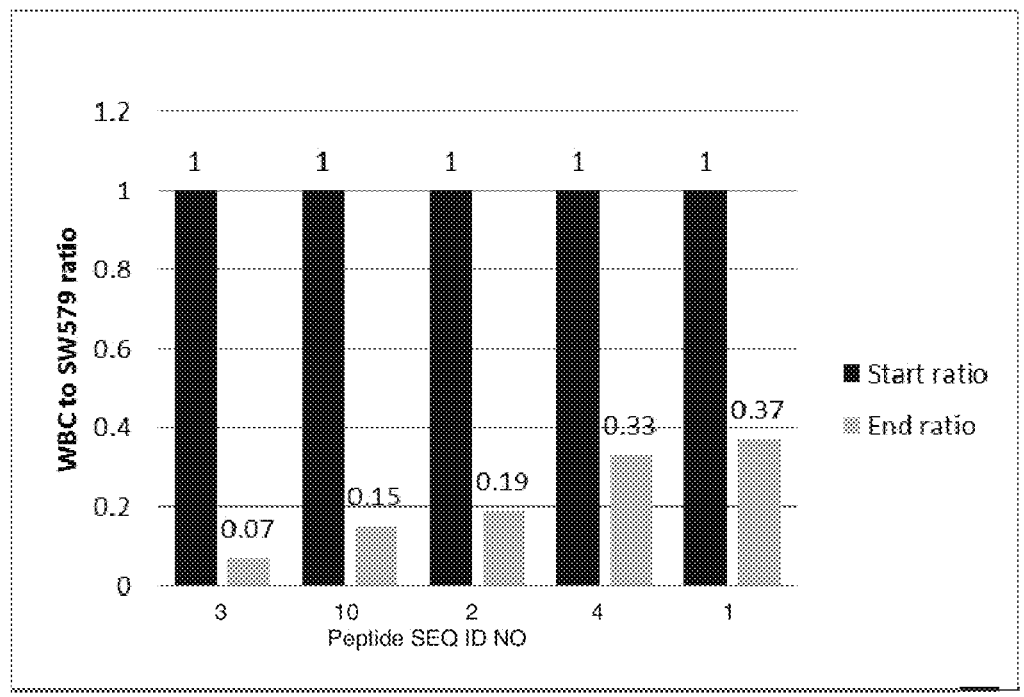

In a first experiment peptides SEQ ID NO: 1, SEQ ID NO: 2, SEQ ID NO: 3 and SEQ ID NO: 4 were tested and peptide SEQ ID NO: 10 was used as a positive control. Panel A of FIG. 9 shows absolute cell capture. Panel B of FIG. 9 shows the change in cell ratio following cell capture on the slide. Human WBC and thyroid cancer SW579 cells were labeled with different CELLTRACKER dyes, mixed at 1 to 1 ratio and applied to a slide with discrete areas coated with peptides. The slide was washed of unbound cells and captured cells were counted under a fluorescent microscope. Data are presented as cell number per microscope field at 100× magnification averaged from 8 fields. Slide area not coated with peptide was used as a negative control. Preferential capture of SW579 cells was observed leading to depletion of WBC up to 93%. Tested peptides differed in capture selectivity with SEQ ID NO: 3 and SEQ ID NO: 2 being more selective (lower WBC to SW579 end ratio) than SEQ ID NO: 4 and SEQ ID NO: 1. Thus the degree of WBC removal from the diagnostic sample can be controlled by using a peptide most suitable for the application.

FIGS. 10A-10C show selective capture of thyroid cancer cells using peptide SEQ ID NO: 3. Specifically, a sample of thyroid cancer cells was spiked with whole blood to model a bloody fine needle aspirate sample, a common challenge in fine needle aspiration biopsies. Cells were applied to a slide coated with peptide SEQ ID NO: 3 or slides not coated with peptide. Panel A of FIG. 10 shows cells applied to a slide without peptide, slide not washed. Blood cells are retained on the slide obscuring diagnostic cells. Panel B of FIG. 10 shows cells applied to a slide without peptide, slide washed. Most cells are washed away. Panel C of FIG. 10 shows cells applied to a slide coated with peptide SEQ ID NO: 3, slide washed. Blood cells are washed away and thyroid cells retained. H&E staining, 200× magnification.

Example 9

Figure 11A:
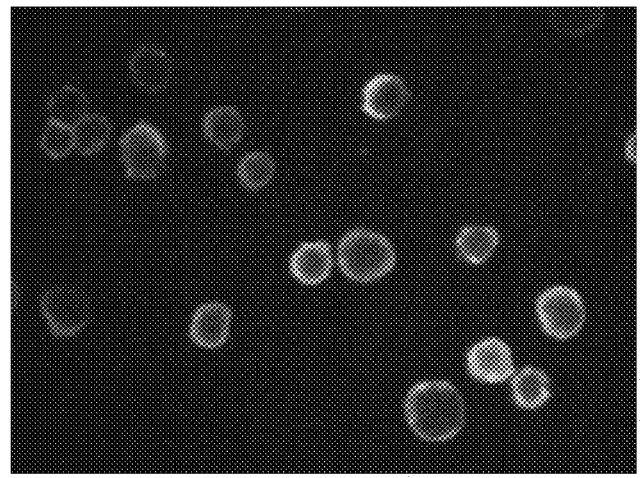
FIGS. 11A-11C are images showing immunocytochemistry for carcinoembryonic antigen expression in J82 urothelial cancer cells captured onto slides functionalized with cell binding peptides according to embodiments of the present disclosure. Images show immunocytochemistry of J82 cells for carcinoembryonic antigen (CEA) captured onto slide functionalized with A) cell binding peptide SEQ ID NO: 4, B) cell binding peptide SEQ ID NO: 5, and C) cell binding peptide SEQ ID NO: 7 using Alexa 488 and 400× magnification.
Figure 11B:
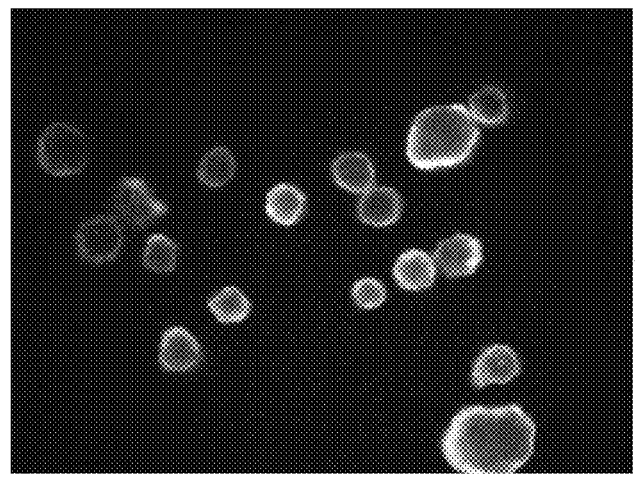
Figure 11C:
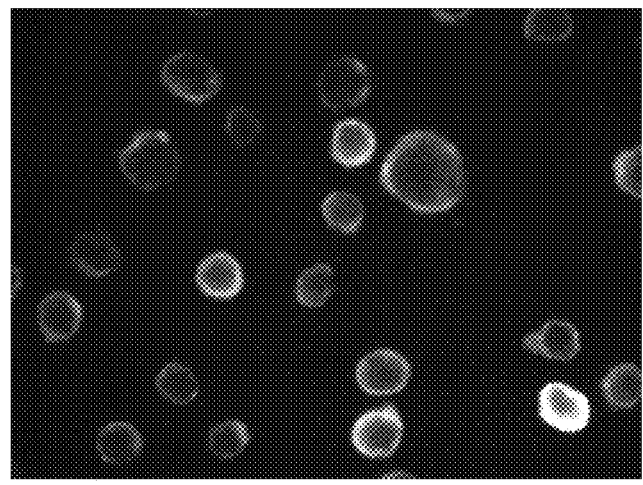

Immunocytochemistry of Urothelial Cancer Cells Captured on Peptide Functionalized Slides NHS slides were functionalized with peptide SEQ ID NO: 4, SEQ ID NO: 5, or SEQ ID NO: 7. J82 urothelial cancer cells were applied to the peptide functionalized slide in cell capture buffer. Following 15 min incubation, the slide was washed in wash buffer to remove unbound cells. The slide was fixed in paraformaldehyde, dried, and subjected to immunostaining with rabbit IgG anti-carcinoembryonic antigen (CEA) antibody (ABCAM). The staining was followed by incubation with a secondary antibody, goat anti-rabbit labeled with Alexa Fluor 488. The slide was counterstained with DAPI to visualize cell nuclei and cover slipped with fluorescent mounting medium. Images were taken at 400× magnification in a green fluorescence filter for Alexa 488 or blue filter for Dapi. The resulting images are shown in FIGS. 11A-11C. Panel A shows image using SEQ ID NO: 4, panel B shows image using SEQ ID NO: 5, and panel C shows image using SEQ ID NO: 7. The cells demonstrated strong green signal indicating expression of CEA, a common cancer marker, proving suitability of cells captured on peptides for immunocytochemistry. Cells captured on peptide and stained in the absence of the primary anti-CEA antibody were used as negative control. No green signal was observed in those images.

One skilled in the art will readily appreciate that the present disclosure is well adapted to carry out the objects and obtain the ends and advantages mentioned, as well as those inherent therein. The present Examples along with the methods described herein are presently representative of preferred embodiments, are exemplary, and are not intended as limitations on the scope of the invention. Changes therein and other uses will occur to those skilled in the art which are encompassed within the spirit of the present disclosure as defined by the scope of the claims.

References

All publications, patent applications, patents, and other references are herein incorporated by reference to the same extent as if each individual publication, patent application, patent, and other reference was specifically and individually indicated to be incorporated by reference. It will be understood that such reference does not constitute an admission that any of these documents form part of the common general knowledge in the art.

1. Sullivan, P. S., Chan, J. B., Levin, M. R., and Rao, J., *Urine cytology and adjunct markers for detection and surveillance of bladder cancer.* Am J Transl Res, 2010. 2(4): p. 412-40.

That which is claimed:

1. A device for capturing cells, the device comprising a support having an attached cell binding peptide for binding to and capturing cells, wherein the peptide comprises a sequence as set forth in:
   a. SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10;
   b. a conservatively substituted variant having at least 70% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10; or
   c. a variant having at least 70% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

2. The device of claim 1, wherein the support comprises glass, metal, plastic, synthetic matrix, silica gel, polymer, or derivatives or combinations thereof.

3. The device of claim 1, wherein the support is in the form of slides, beads, magnetic beads, microtiter plates, cell culture plates, mesh, fibrous form, hollow fibers, or sheets.

4. The device of claim 1, wherein the cell binding peptide comprises one or more modifications to the peptide N-terminus, peptide C-terminus, or within the peptide amino acid sequence, wherein the modification is one or more of acetyl group, aldehyde group, hydroxyl group, thiol group, amino group, biotin, amino acids, lysine, cysteine, glycine-serine-serine-glycine (GSSG; SEQ ID NO: 11), polymers, synthetic polymers, polyethers, poly(ethylene glycol) ("PEG"), an 11 unit polyethylene glycol ("PEG10"), a 1 unit polyethylene glycol ("mini-PEG" or "MP"), or combinations thereof.

5. The device of claim 4, wherein one or both of an amine group of the peptide N-terminus and an internal lysine amine group of the peptide comprises the acetyl group modification.

6. The device of claim 4, wherein the peptide C-terminus comprises the modification PEG10 linked to lysine, mini-PEG linked to lysine, GSSG (SEQ ID NO: 11) linked to lysine, or GSSG (SEQ ID NO: 11) linked to cysteine.

7. The device of claim 1, wherein the support is in the form of a slide.

8. The device of claim 7, wherein the slide is a N-Hydroxysuccinimide (NHS)-derivatized glass slide, and wherein the cell binding peptide is attached to the slide through a bond between a C-terminal lysine on the peptide and the NHS group on the slide.

9. The device of claim 7, wherein the slide is an epoxy-derivatized glass slide, and wherein the cell binding peptide is attached to the slide through a bond between a C-terminal cysteine on the peptide and the epoxy group on the slide.

10. The device of claim 7, wherein the slide is for evaluation of the captured cells for one or both of bladder cancer and thyroid cancer.

11. A method for capturing cells, the method comprising:
    contacting a sample from a subject that comprises cells with the device of claim 1 having the support with attached cell binding peptide to bind to and capture cells, wherein the contacting is performed under conditions such that the cells are captured onto the support through binding to the cell binding peptide.

12. The method of claim 11, wherein the cell binding peptide binds to one or both of urothelial cells and thyroid follicular cells, and wherein the captured cells are for cytological evaluation for one or both of bladder cancer and thyroid cancer.

13. The method of claim 11, wherein the support is in the form of a slide.

14. The method of claim 11, wherein the support comprises glass, metal, plastic, synthetic matrix, silica gel, or polymer, derivatives or combinations thereof.

15. The method of claim 11, wherein the sample comprises blood, plasma, urine, or fine needle aspirate.

* * * * *

```
                            SEQUENCE LISTING

<160> NUMBER OF SEQ ID NOS: 10

<210> SEQ ID NO 1
<211> LENGTH: 19
<212> TYPE: PRT
<213> ORGANISM: Artificial Sequence
<220> FEATURE:
<223> OTHER INFORMATION: Synthetic sequence

<400> SEQUENCE: 1

Ser Ser Phe Ser Asn Tyr Asp Ser Pro Trp Gly Pro Asn Trp Ser Val
1               5                   10                  15

Ile Ser Arg

<210> SEQ ID NO 2
<211> LENGTH: 19
<212> TYPE: PRT
<213> ORGANISM: Artificial Sequence
<220> FEATURE:
<223> OTHER INFORMATION: Synthetic sequence

<400> SEQUENCE: 2

Ser Ser Ile Glu Asp Leu Pro Lys Asp Trp Pro Leu Phe Gly Trp Met
1               5                   10                  15

Ser Ser Arg

<210> SEQ ID NO 3
<211> LENGTH: 19
<212> TYPE: PRT
<213> ORGANISM: Artificial Sequence
<220> FEATURE:
<223> OTHER INFORMATION: Synthetic sequence

<400> SEQUENCE: 3

Ser Ser Leu Glu Ser Val Lys Glu Pro Trp Gly Pro Gly Trp Ile Pro
1               5                   10                  15

Val Ser Arg

<210> SEQ ID NO 4
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 4

Ser Ser Phe Gly Ser Asp Cys Ser Pro Trp Gly Cys Glu Trp Val Pro
1               5                   10                  15

Val Ser Arg

<210> SEQ ID NO 5
<211> LENGTH: 18
<212> TYPE: PRT
<213> ORGANISM: Artificial Sequence
<220> FEATURE:
<223> OTHER INFORMATION: Synthetic Sequence
```

```
<400> SEQUENCE: 5

Ser Ser Val Ala Leu Ser Phe Gln Ala Val Pro Tyr Asp Phe His Ser
1               5                   10                  15

Ser Arg

<210> SEQ ID NO 6
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 6

Ser Ser Val Gln His Ala Tyr Gln Ala Trp Pro Gly Leu Gly Ala Tyr
1               5                   10                  15

Thr Ser Arg

<210> SEQ ID NO 7
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 7

Ser Ser Leu Phe Val Ala Tyr Pro Asp Ser His Arg Val Trp Asn Val
1               5                   10                  15

Ser Arg

<210> SEQ ID NO 8
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 8

Ser Ser Phe Ile Glu Glu Ser Phe Gln Leu Leu Arg Gly Leu His Gln
1               5                   10                  15

Ser Arg

<210> SEQ ID NO 9
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 9

Ser Ser Phe Asn Ser Asp Ser Trp Leu Trp Ala Tyr Ser Leu Gln Ala
1               5                   10                  15

Glu Ser Arg

<210> SEQ ID NO 10
<211> LENGTH: 17
<212> TYPE: PRT
<213> ORGANISM: Artificial Sequence
<220> FEATURE:
<223> OTHER INFORMATION: Synthetic Sequence
```

```
<400> SEQUENCE: 10

Ser Phe Cys Pro Ser Asn His Asp Cys Ile Asp Trp Phe Ile Arg Ser
1               5                   10                  15
Arg
```